(12) United States Patent
Studer et al.

(10) Patent No.: US 7,143,630 B2
(45) Date of Patent: Dec. 5, 2006

(54) GAS-MEASURING DEVICE WITH AN ELECTROCHEMICAL SENSOR

(75) Inventors: Matthias Studer, Krummesse (DE); Robert Kessel, Bad Oldesloe (DE); Andreas Nauber, Lübeck (DE); Kathleen Leahy, Lübeck (DE); Gero Sagasser, Bad Schwartau (DE); Andreas Huth, Lübeck (DE)

(73) Assignee: Dräger Safety AG & Co. KGaA (DE)

( * ) Notice: Subject to any disclaimer, the term of this patent is extended or adjusted under 35 U.S.C. 154(b) by 16 days.

(21) Appl. No.: 10/979,540

(22) Filed: Nov. 2, 2004

(65) Prior Publication Data

US 2005/0155406 A1 Jul. 21, 2005

(30) Foreign Application Priority Data

Jan. 16, 2004 (DE) ...................... 10 2004 002 289

(51) Int. Cl.
*G01N 27/26* (2006.01)
(52) U.S. Cl. ....................................... 73/1.02; 204/401

(58) Field of Classification Search ................. 73/1.02, 73/1.03, 1.06, 29.05, 29.04, 23.2; 204/401
See application file for complete search history.

(56) References Cited

U.S. PATENT DOCUMENTS

| 5,055,270 | A | * | 10/1991 | Consadori et al. ............ 422/98 |
| 5,205,151 | A | * | 4/1993 | Shimamura et al. ......... 73/1.02 |
| 5,726,906 | A | * | 3/1998 | Matthiessen et al. ......... 702/22 |
| 5,733,436 | A | * | 3/1998 | Demisch et al. ............ 205/775 |
| 5,858,204 | A | * | 1/1999 | Jambo et al. ................ 205/775 |
| 6,076,389 | A |   | 6/2000 | Kaneko |
| 6,693,547 | B1 | * | 2/2004 | Manakkal ................. 340/636.1 |
| 2005/0098447 | A1 | * | 5/2005 | Broy et al. .................. 205/775 |

FOREIGN PATENT DOCUMENTS

DE          44 45 947          6/1996

* cited by examiner

*Primary Examiner*—Robert Raevis
(74) *Attorney, Agent, or Firm*—McGlew & Tuttle, PC

(57) ABSTRACT

A gas-measuring device has an electrochemical sensor and features such that the readiness for use is guaranteed for a determined period of time. A status display (7), is activated by the evaluating circuit (3) of the gas-measuring device. The status display (7) displays the degree of depletion of the sensor.

20 Claims, 4 Drawing Sheets

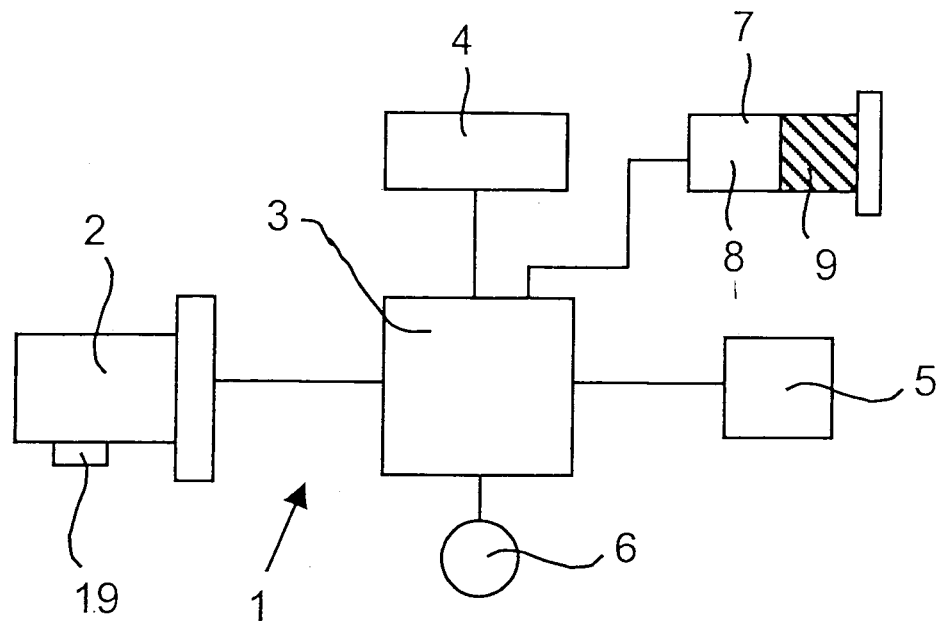
Fig. 1
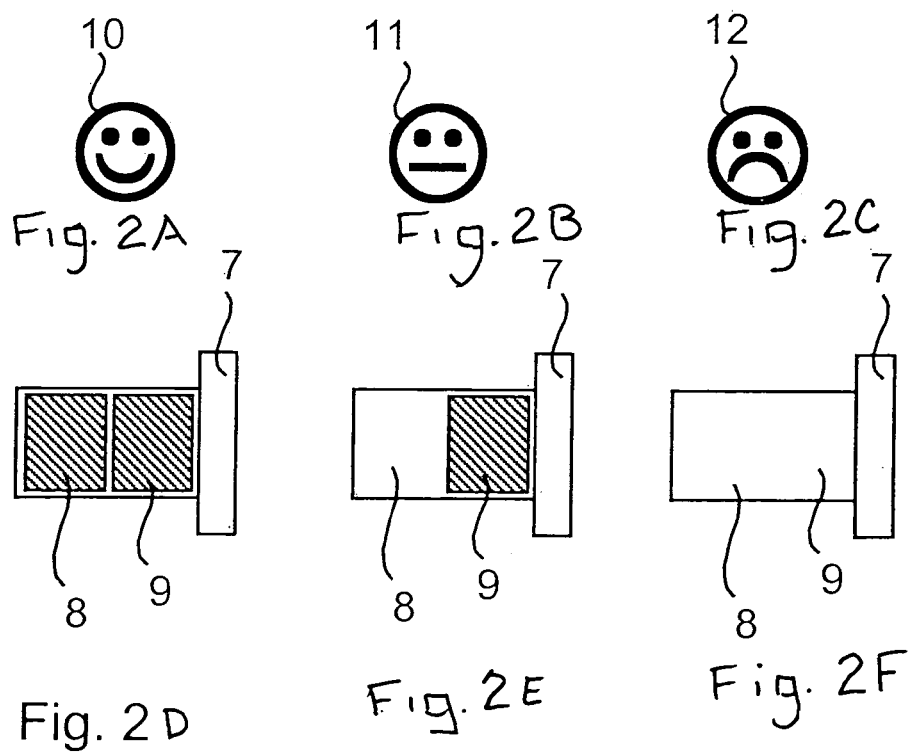

GAS-MEASURING DEVICE WITH AN ELECTROCHEMICAL SENSOR

CROSS REFERENCE TO RELATED APPLICATIONS

This application claims the benefit of priority under 35 U.S.C. § 119 of DE 10 2004 002 289.5 filed Jan. 16, 2004, the entire contents of which are incorporated herein by reference.

FIELD OF THE INVENTION

The present invention pertains to a gas-measuring device with an electrochemical sensor.

BACKGROUND OF THE INVENTION

Electrochemical sensors, especially electrochemical gas sensors, usually do not have an unlimited service life. A point in time at which the technical properties are no longer sufficient for accomplishing the measuring task is reached at a certain time. In electrochemical gas sensors, one of these properties may be, for example, the level of the output signal at a certain gas concentration. Such sensors should therefore be exchanged and replaced with new ones at certain intervals.

Both a safety engineering aspect and an economic aspect play a role concerning the point in time at which the replacement is necessary. From a purely safety engineering viewpoint, the sensor would be replaced at the shortest possible intervals (for example, yearly or more frequently) in order to rule out a failure with the highest possible probability. The drawback of doing so is that needlessly high costs are incurred.

From a purely economical viewpoint, a sensor would be replaced only when it was recognized as being defective. This defect may be determined during the calibration or also during a sensor self-test. The drawback here is that the measuring function is not guaranteed continuously, because replacement of the sensor cannot always be carried out in a short time.

A process for recognizing sources of error in amperometric measuring cells is known from DE 44 45 947 C2. The voltage of the potentiostat is slightly detuned here in order to calculate from this parameters that provide information on the state of use of the electrochemical sensor. It is displayed whether a sensor has been used up or damaged. However, the prior-art process provides no information on how long the sensor can still be used for measurement purposes.

SUMMARY OF THE INVENTION

The basic object of the present invention is to improve a gas-measuring device with an electrochemical sensor such that the readiness for use is guaranteed over a predetermined period of time.

According to the invention, a gas-measuring device is provided with an electrochemical sensor. An evaluating circuit is provided for processing sensor-specific measured variables. A status display is provided that is activated by the evaluating circuit for displaying the sensor depletion.

The advantage of the present invention is essentially that a status display, which displays the degree of depletion of the sensor to the user, is generated at the gas-measuring device on the basis of sensor-specific measured variables. The user thus obtains information on the optimal point in time for the replacement of the sensor. The measuring function of the gas sensor can thus be utilized over the longest period of time possible. The status display described in the present invention is not limited to electrochemical sensors, but it can also be used in case of catalytic or optical gas sensors or electrochemical systems such as batteries.

A trend curve is advantageously determined as a function of time in the evaluating circuit as a function of sensor-specific measured variables and compared with a predetermined limit value. The status display is activated when the function value of the trend curve has reached a predetermined limit value. It is useful in this connection to set a plurality of limit values, which are associated with individual status displays. The course of the trend curve can thus be followed better.

The sensor current is suitable for use as the sensor-specific measured variable in an amperometric fuel cell, the trend curve being formed by integration of the sensor current over time. The value of the integral of a brand new sensor, hereinafter called the current integral, is zero. The depletion of the sensor is also zero here, i.e., the sensor is suitable for use without restrictions. The closer the current integral comes to a predetermined limit value in the course of the use of the sensor, the greater will be the depletion of the sensor up to the complete consumption of the electrolyte or the anode material.

The reduction of the sensor sensitivity E, which assumes the maximum in the original state and steadily declines during the use of the device, is suitable for use as an alternative trend curve. The sensor sensitivity can be determined, for example, during the calibration cycles to be carried out routinely, and a compensating straight line is drawn through the individual measured values. The decline in the sensor sensitivity E from the maximum to a predetermined lower limit value is an indicator of the depletion of the sensor or of the complete depletion of the sensor.

A temperature sensor measuring the ambient temperature is expediently provided, and positive deviations and negative deviations from a mean temperature $T_M$ are provided as additional measured variables. Integrals of the positive temperature deviations and negative temperature deviations are then formed. The temperature sensor may be arranged either at the gas-measuring device itself or at the sensor.

Exemplary embodiments are shown in the drawings and will be explained in greater detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

BRIEF DESCRIPTION OF THE DRAWINGS

FIG. 1 is a schematic view of the design of a gas-measuring device according to the present invention;

FIG. 2A is a view of one of different information states of a of a status display;

FIG. 2B is a view of another of different information states of a status display;

FIG. 2C is a view of another of different information states of a status display;

FIG. 2D is a view of another of different information states of another status display;

FIG. 2E is a view of another of different information states of the another status display;

FIG. 2F is a view of another of different information states of the another status display;

DESCRIPTION OF THE PREFERRED EMBODIMENTS

Figure 3A:
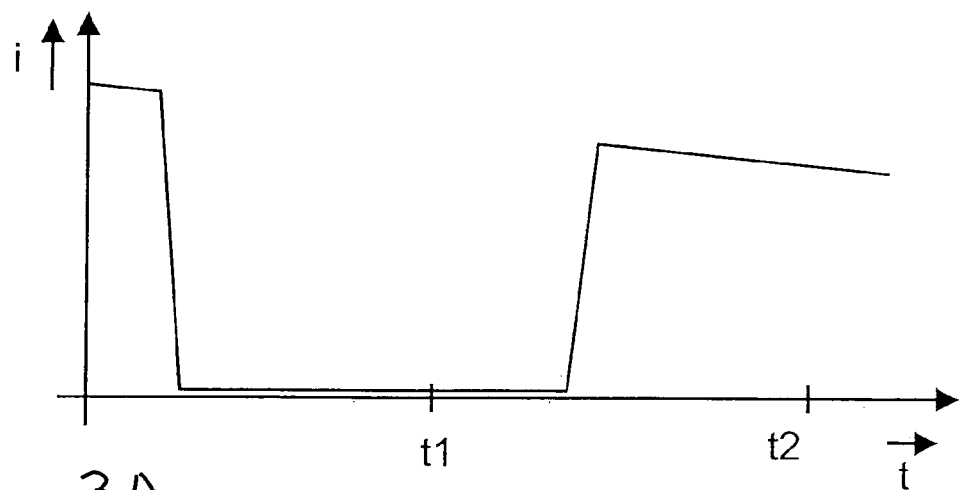
FIG. 3A is an example of the evaluation of the sensor current showing the course of sensor current as a function of time.

FIG. 1 schematically illustrates a gas-measuring device 1 with an amperometric fuel cell as the sensor 2, an evaluating circuit 3 for processing sensor-specific measured variables, a display unit 4 for measured values of a power supply unit 5, a temperature sensor 6 and with a status display 7 for the sensor depletion. The status display 7 has two display fields 8, 9, which are black or neutral depending on the state of the sensor. Only the display field 9 is blackened in the sensor state shown in FIG. 1, which approximately corresponds to a sensor 2 having been consumed by more than half and still has a high readiness for use with low failure probability.

FIGS. 2A–2E show different information states of the status display 7. FIG. 2D (the left-hand view) shows two blackened display fields 8, 9 that represent an unconsumed sensor 2 with a very high readiness for use and very low failure probability. In contrast, FIG. 2F (the right-hand view of the status display 7) shows two unblackened display fields 8, 9 that illustrates a sensor 2 that has only a limited readiness for use and should be replaced. FIG. 2E (the view in the middle) corresponds to a sensor state that is between these two trend values. As an alternative, the status display may also be performed with symbols "good 10" (FIG. 2A), "medium 11" (FIG. 2B) and "poor 12" (FIG. 2C).

One possibility of determining the depletion of the sensor is to form the integral of the sensor current as a function of time.

Figure 3B:
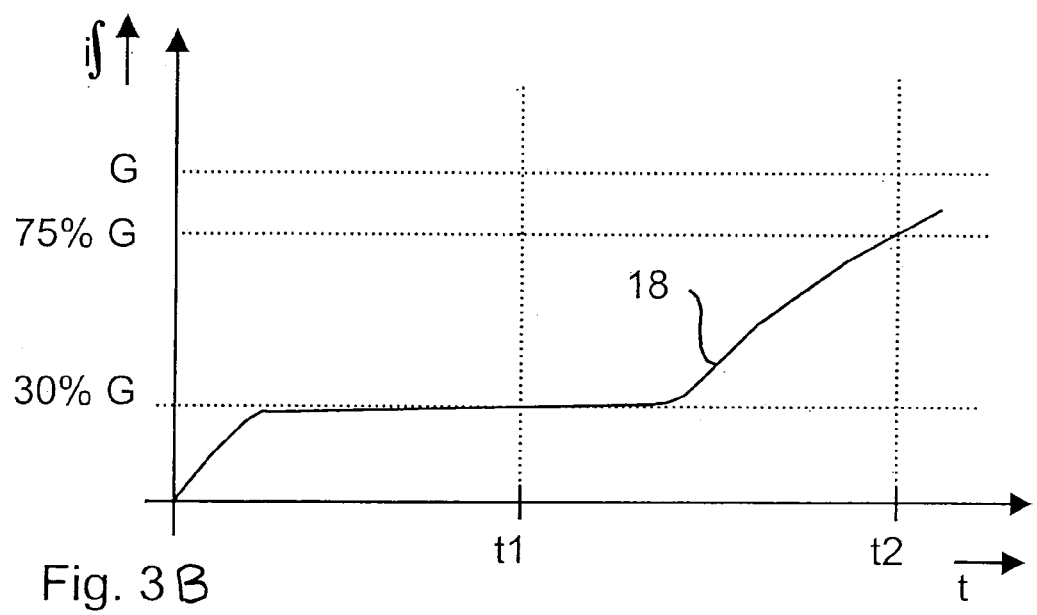
FIG. 3B is an example of the evaluation of the sensor current showing the course of the integral of sensor current.

The upper part of FIG. 3 illustrates the course of the sensor current as a function of time t; i=i(t). The time axis begins with t=0 for an unconsumed sensor 2. The value of the sensor current i(t) depends on the gas concentration to be measured. No gas to be detected is present in the middle range of the curve, and the sensor current i drops to zero. When gas is admitted with constant gas concentration, the sensor current i increases steadily in an amperometric fuel cell until the sensor 2 is consumed completely because of the electrochemical reaction with the gas sample.

The lower part of FIG. 3 shows the course of the integral of the sensor current i, the current integral 18, as a function of the time t. The current integral 18 begins at the time t=0 with zero value for a brand new, unconsumed sensor 2. A limit value G, at which the sensor 2 is consumed, is set for the current integral 18. This limit value G is determined by experiments for a certain type of sensor. Percentages of the limit values, 30% G and 75% G, are set as the criterion for the extent of the sensor depletion.

Both display fields 7, 8 of the status display 7 are blackened at the time t=0 in case of an unconsumed sensor 2. Only the display field 9 is active if the current integral 18 reaches the limit value 30% G at the time t=$t_1$. When the 75% G limit value is exceeded at the time t=$t_2$, the display field 9 goes out as well and the sensor 2 must be replaced.

As an alternative to the current integral 18 or in addition to the current integral 18, the sensor sensitivity E can be used as a criterion for the degree of depletion of the sensor. The sensitivity of the sensor is determined during calibration cycles to be performed regularly and is obtained from the quotient of the signal rise and the change in the gas concentration.

Figure 4:
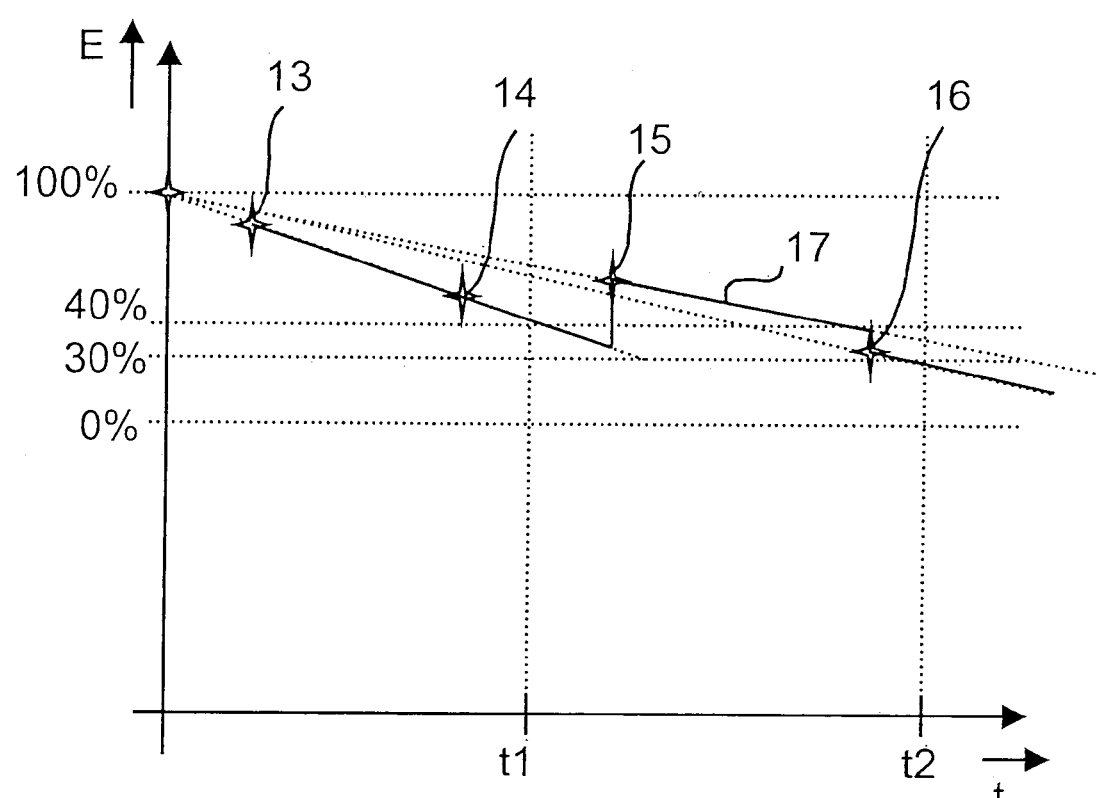
FIG. 4 is an example of the evaluation of the sensor sensitivity.

FIG. 4 illustrates the course of the sensor sensitivity E as a function of the duration of use t. The sensor sensitivity E is determined for the first time at the time t=0 for a brand new sensor 2 and is set at 100%. Extrapolation lines are drawn through additional measured values 13, 14, 15, 16 determined within the framework of calibrations. The compensation line 17 shows the decline of the sensitivity E as a function of the duration of use t. Only 40% of the original sensitivity E is present at the time t=$t_1$, whereas the sensitivity has dropped to 30% of the initial value at the time t=$t_2$.

The sensor sensitivity E has its maximum at the time t=0, and both display fields 8, 9 of the status display 7 are blackened. If the sensor sensitivity E has dropped to 40% E at the time t=$t_1$, only the display field 9 is active. If the sensor sensitivity E drops below the value 30% E at the time t=$t_2$, none of the display fields 8, 9 is active, and the sensor 2 must be replaced.

If the sensor 2 is exposed to temperature effects, the ambient temperature must be taken into account for the evaluation of the depletion of the sensor.

Figure 5A:
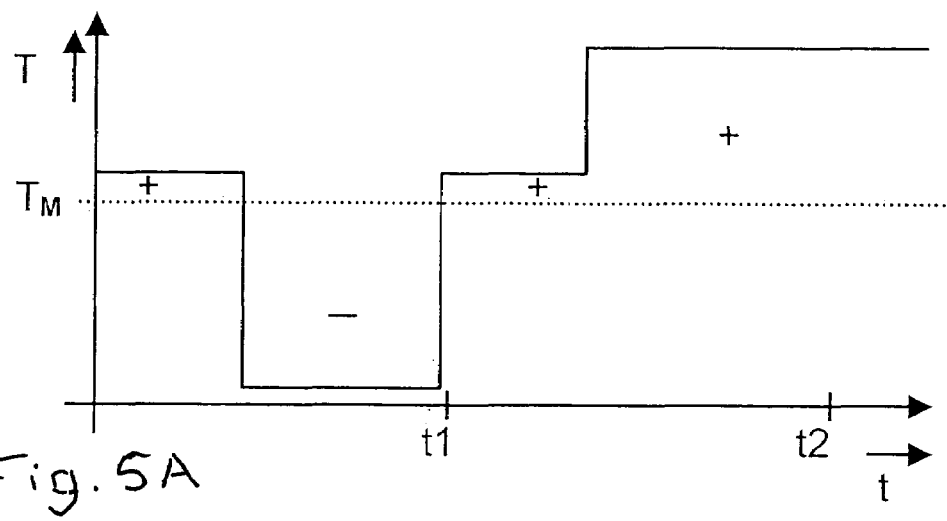
FIG. 5A is an example for taking into account the temperature effect showing the course of the ambient temperature as a function of time.
Figure 5B:
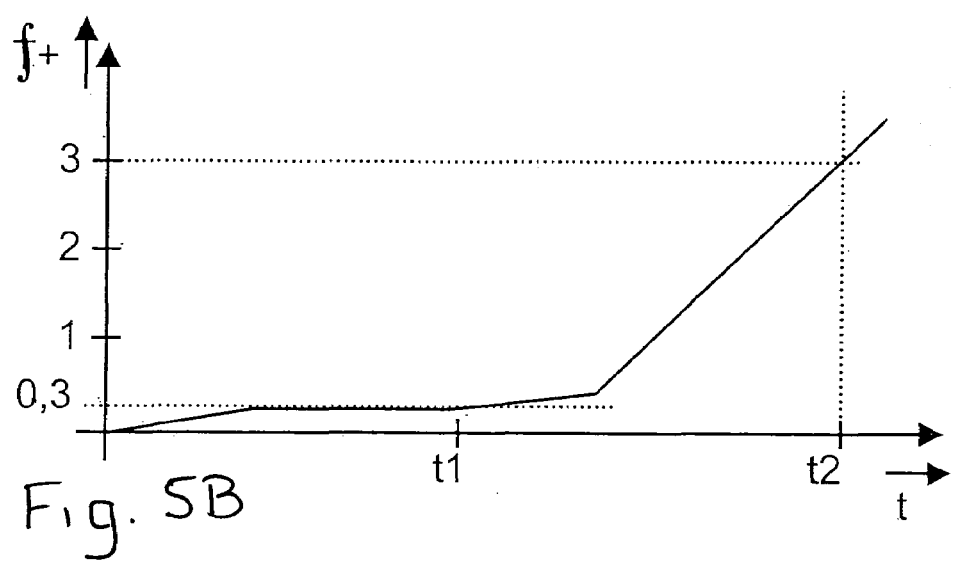
FIG. 5B is an example for taking into account the temperature effect showing the integral of positive temperature deviations.
Figure 5C:
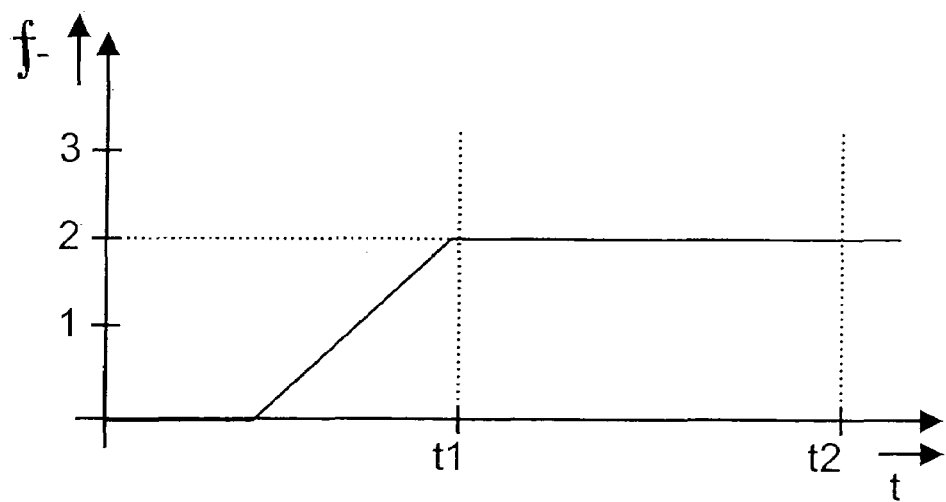
FIG. 5C is an example for taking into account the temperature effect showing the integral of negative temperature deviations.

FIGS. 5A–5C show an example for taking into account the temperature effect.

The upper curve (FIG. 5A) illustrates the course of the ambient temperature T as a function of the time t. The temperature $T_m$ favorable for the operation of the sensor is taken from the sensor specification and used as a reference line for the temperature evaluation. Positive deviations, designated by "plus," and negative deviations, designated by "minus," are integrated in separate integrals as a function of time. Positive temperature deviations usually shorten the duration of use of the sensor 2 more greatly than do negative temperature deviations.

The middle curve (FIG. 5B) shows the integral of the positive temperature deviations, while the lower curve (FIG. 5C) represents the integral of the negative temperature deviations. Factors that affect the determination of the status of the sensor are determined from the temperature integrals at the times $t_1$ and $t_2$. The higher the values of the temperature integrals at the times $t_1$ and $t_2$, the more greatly are the limit values reduced at which the status display 7 with two blackened 8, 9 jumps over to a blackened display field 9 or the display for the sensor replacement, for which case no display field 8, 9 is active, is reached already earlier in time at the corresponding times of the current integral 18 according to FIG. 3B or the compensating lines 17 for the sensor sensitivity E according to FIG. 4. The status data of the sensor 2 are stored in an auxiliary memory 19 arranged at the sensor 2 in order to make it possible to also determine the status of the sensor 2 when this was used at different devices.

While specific embodiments of the invention have been shown and described in detail to illustrate the application of the principles of the invention, it will be understood that the invention may be embodied otherwise without departing from such principles.

What is claimed is:

1. A gas-measuring device, comprising:
an electrochemical sensor;
an evaluating circuit for processing sensor-specific measured variables, said evaluating circuit processing at least one sensor-specific measured variable to generate a trend curve over a lifetime of said sensor, said measured variable being sensor current and said trend curve is a current integral of the sensor current; and
a status display activated by the evaluating circuit for displaying the sensor depletion as a function of one of the sensor specific measured variables, and said status display being activated when said trend curve reaches predetermined limit values, said status display providing three indicators showing different degrees of depletion of said sensor, said indicators being activated when said trend curve reaches said predetermined limit values.

2. A gas-measuring device in accordance with claim 1, wherein another said measured variable is sensor sensitivity and another trend curve is generated as a compensating line through individual measured values of the sensor sensitivity.

3. A gas-measuring device in accordance with claim 1, wherein the status display is present as a bar graph display with display fields or as a symbol representation with symbols representing good, medium and poor sensor readiness.

4. A gas-measuring device in accordance with claim 1, further comprising a temperature sensor measuring an ambient temperature, wherein positive deviations and negative deviations from a mean temperature $T_m$ are selected as additional measured variables.

5. A gas-measuring device in accordance with claim 4, wherein:
said evaluating circuit changes said limit values based on said positive deviations from said mean temperature.

6. A gas-measuring device in accordance with claim 5, wherein:
said evaluating circuit integrates said positive deviations to form a positive temperature deviation integral, said evaluating circuit changes said limit values based on said positive temperature deviation integral.

7. A gas-measuring device in accordance with claim 6, wherein:
said evaluating circuit reduces said limit values as said positive temperature deviation integral increases.

8. A gas-measuring device in accordance with claim 7, wherein:
said evaluating circuit integrates said negative deviations to form a negative temperature deviation integral, said evaluating circuit changes said limit values based on said negative temperature deviation integral;
said evaluating circuit reduces said limit values as said negative temperature deviation integral increases.

9. A gas-measuring system, comprising:
an electrochemical sensor;
an evaluating circuit for processing sensor-specific measured variables, said evaluating circuit processing at least one sensor-specific measured variable to generate a trend curve over a lifetime of the sensor; and
a status display activated by the evaluating circuit when said trend curve reaches a predetermined limit value for displaying a sensor depletion based on said processing of sensor-specific measured variables, said status display providing three indicators showing different degrees of depletion of said sensor, said indicators being activated when said trend curve reaches predetermined limit values;
an auxiliary memory arranged at said electrochemical sensor and storing said trend curve, said auxiliary member and said sensor being separatable as a single unit from said evaluating circuit and said status display for use in other gas-measuring systems.

10. A gas-measuring system in accordance with claim 9, wherein said measured variable is sensor current and said trend curve is a current integral of the sensor current.

11. A gas-measuring system in accordance with claim 10, further comprising a temperature sensor measuring an ambient temperature, wherein positive deviations and negative deviations from a mean temperature $T_m$ are selected as additional measured variables.

12. A gas-measuring system in accordance with claim 11, wherein:
said evaluating circuit changes said limit values based on said positive deviations from said mean temperature.

13. A gas-measuring system in accordance with claim 12, wherein:
said evaluating circuit integrates said positive deviations to form a positive temperature deviation integral, said evaluating circuit changes said limit values based on said positive temperature deviation integral.

14. A gas-measuring system in accordance with claim 13, wherein:
said evaluating circuit reduces said limit values as said positive temperature deviation integral increases.

15. A gas-measuring device in accordance with claim 9, wherein said measured variable is the sensor sensitivity and said trend curve is a line through individual measured values of the sensor sensitivity.

16. A gas-measuring system comprising:
an electrochemical sensor;
an evaluating circuit connected to said sensor and integrating current from said sensor, said evaluating circuit processing the integrated current to calculate sensor depletion;
a status display activated by said evaluating circuit and displaying said sensor depletion when said trend curve reaches predetermined limit values;
a temperature sensor connected to said evaluating circuit and measuring ambient temperature, said sensor having a predetermined favorable operating temperature, said evaluating circuit recording when the ambient temperature is larger than said favorable operating temperature as positive temperature deviations, said evaluating circuit changing said limit values based on said positive deviations.

17. A gas-measuring system in accordance with claim 16, wherein:
said evaluating circuit calculates sensor depletion as being proportional to the integrated current.

18. A gas-measuring system in accordance with claim 16, wherein:
said evaluating circuit integrates said positive deviations to form a positive temperature deviation integral, said evaluating circuit changes said limit values based on said positive temperature deviation integral.

19. A gas-measuring system in accordance with claim 18, wherein:
   said evaluating circuit reduces said limit values as said positive temperature deviation integral increases.

20. A gas-measuring system in accordance with claim 19, wherein:
   said evaluating circuit records when the ambient temperature is less than said favorable operating temperature as negative temperature deviations,
   said evaluating circuit integrates said negative deviations to form a negative temperature deviation integral, said evaluating circuit changes said limit values based on said negative temperature deviation integral;
   said evaluating circuit reduces said limit values as said negative temperature deviation integral increases, reductions of said limit values are greater for equal increases in said positive temperature deviation integral.

* * * * *